United States Patent [19]

Flournoy et al.

[11] 4,022,055
[45] May 10, 1977

[54] PULSE-ECHO METHOD AND SYSTEM FOR TESTING WALL THICKNESSES

[75] Inventors: Norman E. Flournoy; David A. Morris; Robert J. Agnew, all of Richmond, Va.

[73] Assignee: Texaco Inc., New York, N.Y.

[22] Filed: Dec. 2, 1974

[21] Appl. No.: 528,974

[52] U.S. Cl. .......................... 73/67.7; 73/71.5 US; 340/8 FT
[51] Int. Cl.² .................................. G01N 29/00
[58] Field of Search .......... 73/67.7, 67.8 R, 67.8 S, 73/67.9, 67.5 R, 71.5 US; 340/8 FT; 310/8.3, 8.7

[56] References Cited

UNITED STATES PATENTS

| | | | |
|---|---|---|---|
| 3,028,752 | 4/1962 | Bacon | 73/67.8 R |
| 3,106,839 | 10/1963 | Sansom | 310/8.7 |
| 3,192,418 | 6/1965 | Sansom | 73/67.8 R |
| 3,262,307 | 7/1966 | Hart | 73/71.5 US |
| 3,283,294 | 11/1966 | Schrom | 340/8 FT |
| 3,451,260 | 6/1969 | Thurstone | 73/71.5 US |
| 3,550,438 | 12/1970 | Kapluszak | 73/71.5 US |
| 3,599,478 | 8/1971 | Weinbaum | 73/67.7 |
| 3,636,778 | 1/1972 | Huffstetler | 73/67.8 R |

FOREIGN PATENTS OR APPLICATIONS 206,854 1968 U.S.S.R. .......... 73/71.5 US

OTHER PUBLICATIONS

Materials Evaluation, "Using Mirrors To Do The Impossible," pp. 48A, 50A, May 1973.

Primary Examiner—Richard C. Queisser
Assistant Examiner—Stephen A. Kreitman
Attorney, Agent, or Firm—Thomas H. Whaley; Carl G. Ries; Henry C. Dearborn

[57] ABSTRACT

A method and system for improving the pulse-echo type of testing to determine wall thicknesses. It is particularly applicable to pipes. There is a pulse directed transversely to the wall so that reflections from the inner and outer surfaces will indicate the thickness, and another pulse is directed at an angle to the wall with time spacing. The angled pulse path permits penetration so that the presence of an undesirable type of discontinuity will cause an additional reflection which distinguishes this type of discontinuity.

4 Claims, 13 Drawing Figures

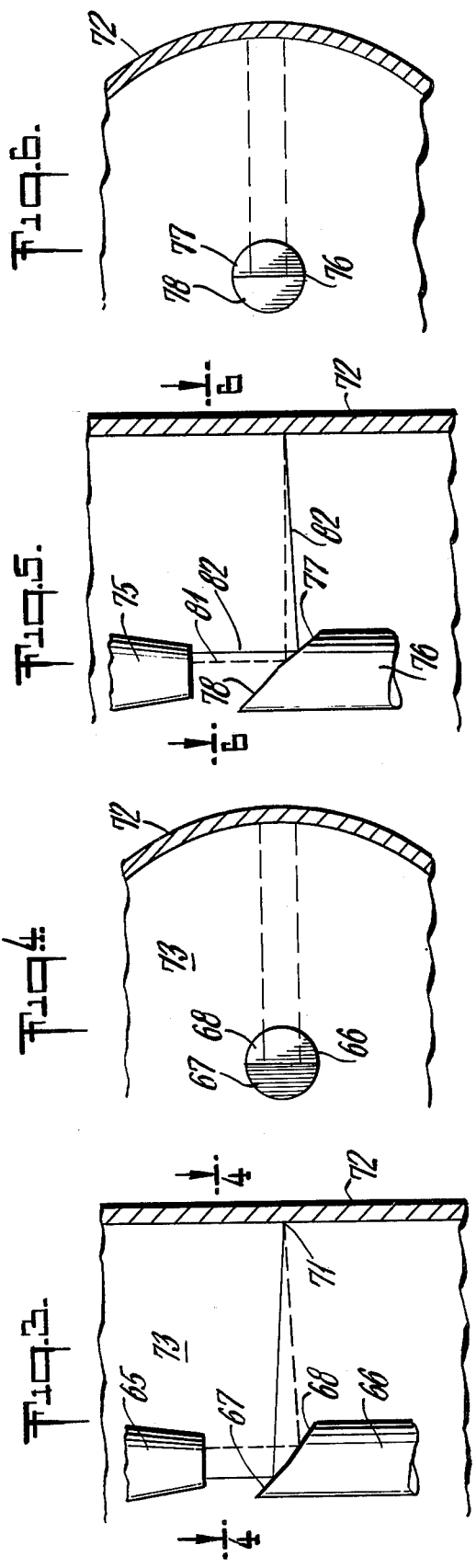

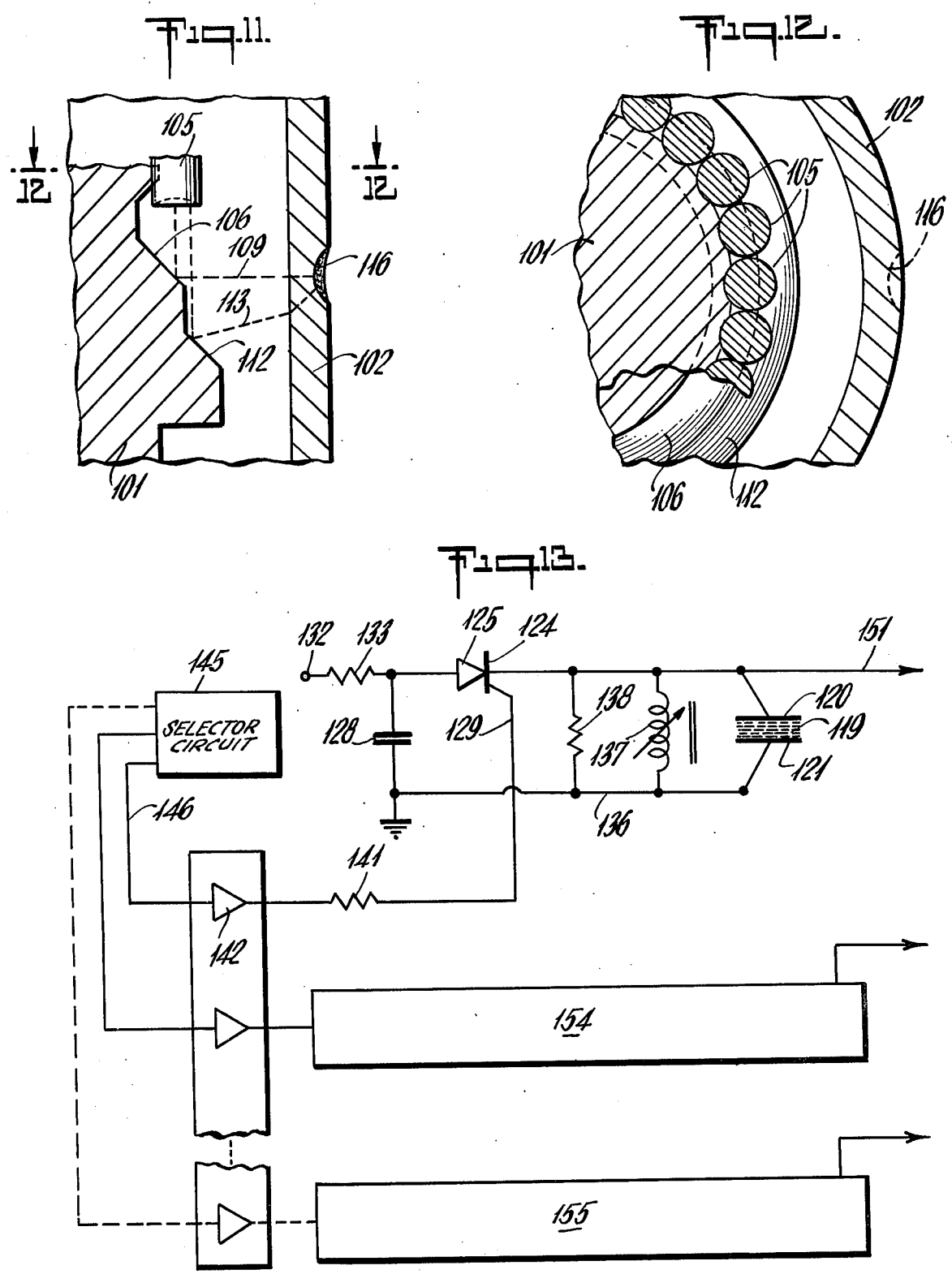

PULSE-ECHO METHOD AND SYSTEM FOR TESTING WALL THICKNESSES

BACKGROUND OF THE INVENTION

1. Field of the Invention

This invention concerns pulse-echo type wall thickness measuring in general. More specifically, it relates to a method and system for improving upon known pulse-echo types of wall thickness measurement.

2. Description of the Prior Art

In the field of non destructived testing, or measuring of thickness of the walls of elongated bodies, use has been made of a longitudinally directed pulse transducer with a 45° reflecting surface so as to direct the energy from a parallel direction to one at right angles that is thus transverse to the walls of the elongated body. Also, in connection with pipe line inspection employing pulse-echo systems, it has been known to make use of a plural transducer with rotator, which employed a scanning or a physical rotation at a rate proportional to the longitudinal travel in the pipe. However, neither of the prior arrangements conceived of simultaneously introducing another pulse directed at a different angle relative to the surface of the pipe or other wall. This invention makes use of the latter method in conjuction with known elements and arrangements, to provide for an improved method and system for determining a characterization of a discontinuity so as to be able to recognize a cavity or thin spot, as distinguished from a welded joint or the like.

Thus, it is a object of this invention to provide an improved method or system for measuring wall thickness with a pulse-echo type of system while employing an additional means for characterizing a discontinuity in said wall thickness that may be observed.

SUMMARY OF THE INVENTION

Briefly, the invention concerns a pulse-echo method for testing wall thickness of pipes or the like. It relates to an improvement which comprises transmitting a pulse of energy along a path transverse to said wall, and receiving reflected pulses after reflection of said transmitted pulse from the surfaces of said wall in order to determine the thickness of said wall. It also comprises transmitting another pulse of energy along a path having a angle of incidence relative to said wall that is greater than the critical angle of refraction in order to permit reflected energy from a discontinuity in said wall to be returned along the path of said other pulse. And, it also comprises the step of receiving said other pulse reflection from the discontinuity at a time spaced from said first named reflected pulses in order to characterize said discontinuity.

Again briefly, the invention concerns a pulse-echo method for testing wall thickness of pipes, and it concerns the improvement which comprises the steps of generating a plurality of single pulses sequentially all directed along paths parallel to the axis of said pipe, and reflecting a portion of each of said single pulses from a 45° surface to direct it along a path transverse to said pipe wall. It also comprises the steps of reflecting another portion of each of said single pulses from a surface more than 45° relative to said parallel paths, and receiving reflected pulses returned from said first named portion by the surfaces of said pipe wall in order to determine the thickness of said wall. Finally, it comprises of the step of receiving any reflected pulse returned from said other portion by a discontinuity in said pipe wall, in order to characterize said discontinuity.

Once more briefly, the invention concerns a pulse-echo system for measuring wall thickness of a pipe. It relates to the improvement which comprises in combination a plurality of generating means located space peripherally about the axis and inside of said pipe. The said means is oriented for directing the pulses parallel to the axis of said pipe. It also comprises a first angular reflecting surface having a 45° angle relative to said axis and spaced axially from said pulse generating means. The said first surface extends radially about half the width of said pulses for splitting off a portion of each and directing said portion along a path transverse to the wall of the pipe at that location. It also comprises a second angular reflecting surface having an angle of more than 45° relative to said axis and being spaced axially at a greater distance from said pulse generating means than the first annular surface. The said second surface extends radially the other half of the width of said pulses for directing another portion of each pulse along a path having an angle of incidence relative to the wall of said pipe at that location which is greater than the critical angle of refraction in order to permit any reflected energy from a discontinuity in said wall to be returned along said other portion path.

BRIEF DESCRIPTION OF THE DRAWINGS

The foregoing and other objects and benefits of the invention will be more fully set forth below in connection with the best mode contemplated by the inventors for carrying out the invention, and in connection with which there are illustrations provided in the drawings, wherein:

FIG. 3–4, 5–6, 7–8, and 9–10 are fragmentary schematic showings in elevation and cross section, and plan views, respectively illustrating various modifications as to different configurations of a reflecting surface which may be used in order to control the characteristics of an ultrasonic energy beam;

FIG. 11 is a fragmentary schematic, showing a longitudinal cross-section taken along the lines 11—11 of FIG. 12. It illustrates another form of the invention which is particularly for use in pipe wall thickness measurement;

FIG. 12 is a horizontal cross-sectional view taken along the lines 12—12 of FIG. 11; and FIG. 13 is schematic circuit diagram illustrating an electrical circuit arrangement for use with the combination of elements that are illustrated in FIGS. 11 and 12.

DESCRIPTION OF THE PREFERRED EMBODIMENTS

The pulse-echo technique is well-known in connection with ultrasonic energy, and has been considerably employed with non-destructive testing or measuring of wall thicknesses of various types of material including pipes for use in pipelines, and the like. However, in making use of this technique heretofore it has been found that often there is a difficulty in the ability to distinguish between thin or corroded spots and other anomalies such as welded joints and irregular surfaces. This invention provides a method and system which overcomes such difficulties. It makes it possible to have positive identification of thin or corroded spots in the walls of a pipe or the like.

Figure 1:
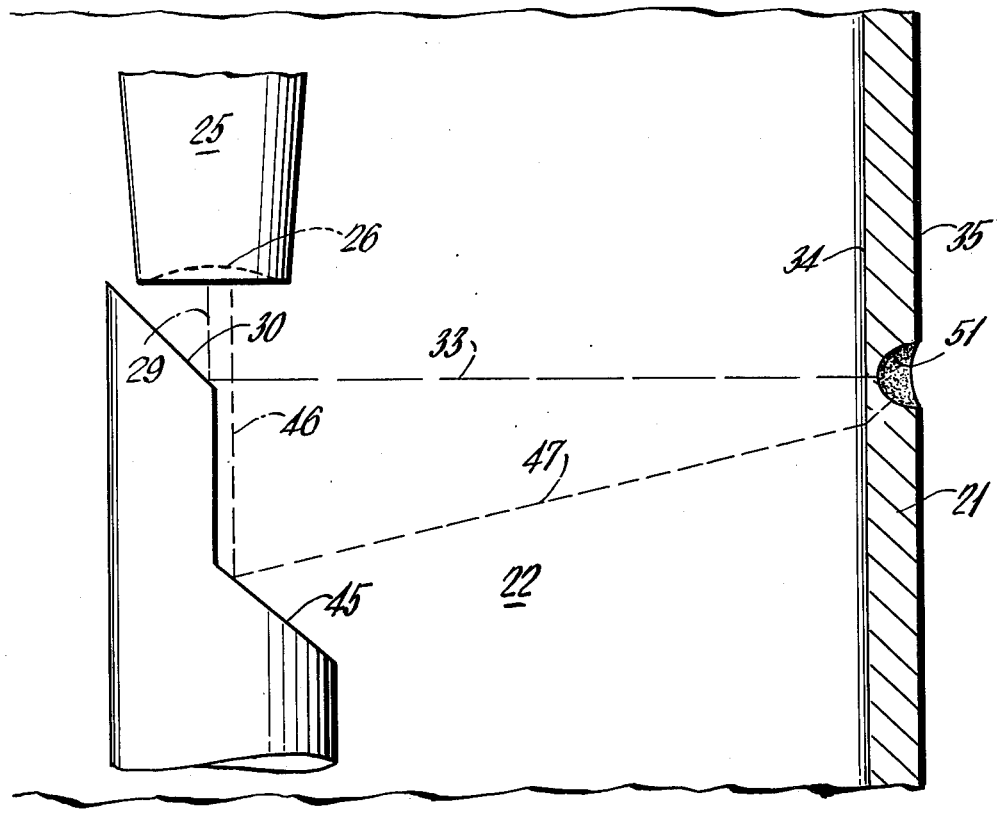
FIG. 1 is a fragmentary schematic showing, partly in elevation and partly in cross section, illustrating one form of apparatus which may be employed with the invention.

Thus, with reference to FIG. 1, there is shown in longitudinal cross-section, a fragemental portion of a pipe 21. It will be appreciated that the wall 21 of the pipe might also be a wall of a tank or the like. Also, it will be understood that inside the pipe 21 there is a fluid 22 which will act as a good conductor for acoustic energy.

In order to measure the thickness of the wall of pipe 21, there is a pulse transducer 25 with a lens 26 for creating a directed beam of energy when the crystal is actived. It will be understood that in this type of system a short time duration, unitary pulse of ultrasonic acoustic energy is created by applying a short time duration electrical voltage to the crystal in a conventional manner. The crystal material is preferably lead metaniobate and in the indicated transducer 25 it will be a flat disc shape (not shown) with silvered faces as its electrodes (not shown). Since the crystal is piezoelectric in nature, it will deform and thus produce an acoustic energy pulse.

Because of the orientation of the transducer 25 and the focusing of the lens 26 the pulse will be directed downward along a path 29 until it strikes a flat reflecting surface 30 that is located at 45° relative to the axis of the pipe 21. The energy of that part of the pulse which strikes the surface 30, will then be reflected at right angles to the path 29 and so travel over a path 33 that is transverse to the surface of the pipe wall 21.

The wall 21 of the pipe has a inner surface 34 and an outer surface 35, each of which is a boundary for the material of the pipe 21 such that a reflection of some of the energy in the acoustic pulse will occur from each of these surfaces. These reflected pulses will then travel back along the same path 33 in the other direction and then will be reflected from the surface 30 to travel upward along path 29 until they strike the crystal in transducer 25, where an electrical signal corresponding to the acoustic pulse will be generated. The technique for thus first producing an acoustic pulse and after the short time involved, producing the electrical pulse signals created by the returning reflected acoustic pulses is well-known, as already indicated, and need not be described in greater detail here.

Figure 2:
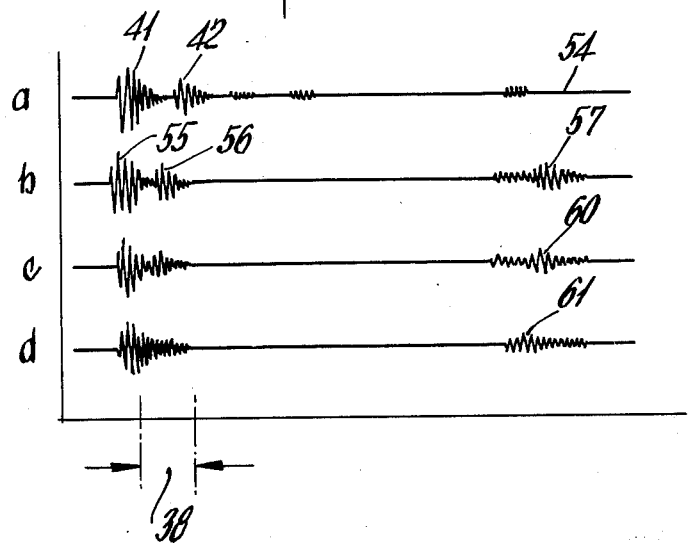
FIG. 2 is an illustration representing oscillographs which show various echo pulse signals which are the reflected pulses that are returned from the surfaces of a wall being measured in the manner indicated by FIG. 1.

FIG. 2 illustrates four lines of corresponding oscillograph records, showing signal amplitudes as a function of time. The energy is ultrasonic in frequency so that the time is short and distance 38 on the time scale represents 3 micro seconds.

The uppermost trace on the FIG. 2 illustration, which is designated by the letter a, shows a pair of reflected pulses 41 and 42. These are the pulse signals generated by the transducer as it responds to the acoustic energy which would have been reflected from the surfaces 34 and 35 of pipe wall 21 if no cavity or other discontinuity existed.

Referring back to FIG. 1 it will be observed that there is another flat reflecting surface 45 spaced somewhat farther away from the transducer 25. This reflecting surface 45 is situated at a angle of more than 45 degrees relative to the axis of the pipe 21. Consequently, energy from pulses travelling over half of the path, e.g. a path 46 that is indicated by a dashed line, will travel over another acoustic path 47. Path 47 has an angle of incidence relative to the inner surface 34 that is greater than the critical angle of refraction for the material of the pipe wall 21. Consequently, this pulse energy will penetrate the surface 34 of the wall of the pipe 21 and travel upward and out without returning unless there is a discontinuity in the pipe wall 21, such as a cavity 51 illustrated. If there is such a discontinuity, there will be a reflected pulse, e.g. from the cavity 51, which will return over the same paths 47 and 46 to impinge upon the transducer 25. It will then generate a reflected pulse in the same manner as the reflected pulses of the thickness measuring paths 33 and 29.

From the foregoing it will be understood that each time the transducer 25 is activated to produce an acoustic pulse, such pulse will travel downward in the fluid 22.

Also, the pulse will have passed through the lens 26 so as to focus it to cover an area that is substantially the same size as the crystal of the transducer 25. As such pulses travel downward from the transducer 25, the upper reflecting surface 30 will reflect half of each pulse at right angles, so that this portion goes transversly to the surfaces 34 and 35 and is reflected from these walls of the pipe 21. The returning reflected pulses thus indicate the thickness of the wall 21.

At a short time thereafter, the reflecting surface 45 will reflect the other half of each pulse so that this portion goes along the path 47 that transmits the energy into the wall 21. Such energy travelling in the wall 21 will cause a reflected return pulse only in the event that there is some discontinuity in its path. Such a discontinuity will cause a reflected return pulse to appear.

It will be understood that by having the reflecting surface 45 located farther away from the transducer 25 than the transverse energy reflecting surface 30 at a predetermined distance, it may be readily determined how much time delay is to be expected between the first pair of reflected pulses and the single returning pulse, each along separate paths.

Of particular importance to this invention is the fact that since conditions on the inner and outer walls of the pipe 21 may include some discontinuities which will not cause the delayed single reflected pulse to return, e.g. weld joints or shallow irregularities, such conditions can be distinguished from others. In other words some conditions can cause loss of either or both of the first pair of reflected pulses which determine the thickness of the wall 21, i.e. pulses along path 33. However, the other slightly delayed pulse along path 47 will provide an indication as to the presence of a discontinuity which causes the single reflected pulse to return, e.g. a cavity or similar thin spot.

FIG. 2 illustrates that part of different oscillographs, taken under some of the foregoing conditions which shows the returning reflected pulses. Thus, already indicated above, the line a of the oscillograph illustrates conditions wherein the reflected returning energy pulses 41 and 42 are from the inner and outer surfaces of the pipe wall 21 where there is no cavity or other discontinuity. Consequently there is nothing to return any reflected energy pulse along the other pulse path 47. The absence of such later pulse may be noted at a general location 54 on the trace a.

On the other hand, the trace *b* of FIG. 2 illustrates a first pair of reflected pulses 55 and 56 which are closer together in time and so indicate a thinner wall condition of the pipe 21. In addition, there is a third pulse 57 that is one which has returned over the angled path 47 and thus positivity indicates the presence of a discontinuity such as a cavity 51 which is illustrated in FIG. 1.

Traces *c* and *d* of FIG. 2 illustrate other conditions similar to trace *b*, but with thinner wall conditions. Consequently, the first pair of reflected, i.e. transverse pulses are closer together. However, these traces also illustrate the present of a discontinuity such as the cavity 51, since in each case there is a delayed single reflected pulse 60 and 61 respectively.

Referring to FIGS. 3–10, there are various modifications shown which relate to the structure of reflectors for ultrasonic energy beams. These are expecially applicable to the type of wall thickness measurement under consideration. It is quite feasible to control the shape of the acoustic energy beams involved, by means of determining the shape of the reflector surface. Thus different types of beam shaping may be carried out. For example, in FIGS. 3 and 4 the beam may be concentrated vertically while retaining the same width in a horizontal plane.

FIGS. 3 and 4 illustrate side and plan views of a transducer 65 that transmits pulse beams onto the angled surface of a reflector 66, which has its reflecting surface divided into two halves 67 and 68. These reflecting surfaces 67 and 68 have a small supplementary angle relative to one another so that the beam of energy reflected will be concentrated in the manner indicated, i.e. toward a reflecting point 71 on a wall 72 of a pipe 73.

On the other hand it may be desirable to slightly disperse the beam of the acoustic pulse path vertically, and such is illustrated in FIGS. 5 and 6. There is a transducer 75 that sends its pulses downward toward a reflector 76, which has its reflecting surface divided into two halves making separate surfaces 77 and 78 as indicated. In this case these surfaces have a slight angular difference which creates the dispersal situation. The transmitted beam of acoustic energy is indicated by a dashed line 81, while the returning path is indicated as a solid line 82. It will be observed that the reflected energy from the wall 72 of the pipe returns farther away from the axis of the transducer 75.

FIGS. 7 and 8 illustrate a reflector surface structure for spreading the acoustic beam horizontally and not vertically. In this case there is a transducer 85 that has its beam directed onto a reflector 86. The surface of reflector 86 has its face divided into two halves 87 and 88. These are flat surfaces angled away from one another in a convex manner a few degrees in order to spread the beam of acoustic energy horizontally as indicated in FIG. 8.

FIGS. 9 and 10 illustrate one more embodiment concerning the reflecting surface structure which may be employed. Since the use of flat surfaces on the reflector will cause a separation into two distinct beams, as indicated in FIG. 8, it may be preferable to employ a curved convex surface. This is illustrated in FIGS. 9 and 10 where there is illustrated a transducer 91 that is directing its energy onto the reflecting surface of a reflector 92 which like reflector 86 in FIGS. 7 and 8 is designed to spread the acoustic energy beam horizontally but not vertically. In this case there is a curved surface 93 that is continuously curved in a convex manner to form the spreading affect. However, it will be understood that surface 93 is a cylindrical curved surface with a straight center line situated at 45 degrees, as indicated in the elevation view of FIG. 9.

FIGS. 11, 12 and 13 illustrate a system for providing a multiple transducer arrangement that is particularly useful in an instrument for determining wall thickness of a pipe. Such an instrument is especially useful for surveying a pipe line.

As schematically illustrated in FIGS. 11 and 12, there is an instrument body 101 that has the diameter designed for a proper size to pass through a pipe 102. In order to made a continuous measurement, or survey of the wall thickness of the pipe 102 there is a plurality of pulse generating transducers 105 that are located circumferentially situated on the body 101 of the instrument. These transducers 105 have the axis of each oriented parallel to the axis of the pipe 102.

The pulses generated by each of the transducers 105 are directed down (as illustrated) parallel to the axis of the pipe 102. Consequently, these pulses impinge upon a first annular reflecting surface 106 that has an angle of 45° relative to the pipe axis. This surface 106 extends radially about half of the width of the pulse beams which are transmitted from the transducers 105, so that a portion of each of the pulses are split off and reflected by the surface 106 to travel over a path 109 in each case. It will be understood that these paths are transverse to the surfaces of the pipe wall 102.

Situated axially farther away from the transducers 105, there is another annular reflecting surface 112 that has its surface at a angle which is greater than 45 degrees relative to the axis of the pipe 102. This surface 112 extends radially far enough to encompass the other half of the pulse ray paths of acoustic energy from transducers 105 so that this portion which is split off of the original pulses, will be reflected along somewhat upwardly directed paths 113. Each of these paths 113 has an angle of incidence relative to the wall of the pipe 102, that is greater than the critical angle of refraction so that the pulses of acoustic energy will enter the material of the wall of pipe 102. Then, as explained previously in connection with FIG. 1 and 2, the energy from the pulses travelling over paths 113 will be reflected back over the paths 113 if they encounter a discontinuity such as a cavity 116, illustrated. Such reflected energies will be returned to the transducers 105 where electrical signals will be generated.

By having the instrument 101 constructed with a plurality of transducers, in the manner illustrated in FIG. 11, 12, and 13 the instrument will be especially suitable for being employed in the survey of a pipeline.

In order to employ the instrument 101 to survey the walls of the pipe 102, the transducers 105 will be pulsed sequently around the circumference of the instrument 101. Consequently, as the instrument travels through the pipe 102 there will be a continuous scanning of the walls of the pipe which may, of course, be part of a pipeline. A schematic circuit arrangement for accomplishing this is illustrated in FIG. 13, where it will be observed that each of the transducers 105 includes a piezo-electic crystal 119 that has electrodes 120 and 121 associated therewith for applying a voltage pulse which will generate the acoustic pulse. Thereafter, the crystal 119 and electrodes 120 and 121 will act inversly to generate an electrical signal, in each case, as the reflected return pulse is detected.

Still referring to FIG. 13, it will be understood that in each case the pulse generating circuit includes a circuit connector 123 that leads from the electrode 120 to a controlled electrode 124 of a silicon controlled rectifier 125. The SCR 125 acts to pass a voltage pulse from a charged capacitor 128 to the crystal 119 whenever it is triggered by a signal applied to a circuit 129 to trip the SCR into conduction. The capacitor 128 is maintain charged by a relatively high DC potential, which is maintained at a terminal 132, with a resistor 133 between the terminal 132 and the high potential plate of capacitor 128.

It will be understood that throughout this specification wherever the abbreviation SCR is employed it stands for silicon controlled rectifier. Such abbreviation is well known to one skilled in the electronic arts.

Referring to the pulse generating circuit of FIG. 13 again, it will be noted that there is a common gound circuit 136 that is connected to the other electrode 121 of the crystal 119. Also, the circuit 136 has one side of a variable inductor 137, as well as one end of a resistor 138 connected thereto. In addition, there is a resistor 141 that is in the control circuit 129. The control circuit goes via a resistor 141 from the output of an amplifier 142. And, the output of a selector circuit 145 goes to the input of the amplifier 142 over a circuit connection 146.

It will be understood that after each acoustic pulse is transmitted, a sufficient period of time is allowed before the next one so as to permit the reflected pulses travelling over the transverse paths 109, in addition to those which may return over the angled path 113 to reach the crystal 119 of the transducer. Also, it will be understood that a circuit connection 151, which goes to an amplifier (not shown), will carry the electrical signals generated by the crystal 119 to such amplifier, from which they may go to an oscilloscope (not shown) or otherwise be used to develop oscillograph signals like those illustrated in FIG. 2.

It will appreciated that there is an individual control and reflected-pulse amplifier circuit for each of the transducers 105. This is indicated in FIG. 13 where there are rectangles 154 and 155 which represent additional circuits like that described above in connection with the crystal 119. There will, of course, be one such circuit for each of the transducers 105.

It will also be understood that the time elements involved in sending and receiving individual acoustic pulses and reflected return pulses, are relatively short as indicated above in connection with FIG. 2. Conquently, a complete scan made be carried out around all of the transducers 105 rapidly enough to provide adequate testing of pipe wall conditions along a pipeline where a normal speed of travel of the instrument through the pipeline is maintained.

METHOD STEPS

A method according to this invention may be carried out by various and different types of apparatus which are not necessarily equivalent to one another. The method relates, in general, to the field of pulse-echo measurement for testing of wall thicknesses, and the following steps should not be considered as limiting the invention or are they necessarily always carried out in the order recited.

A first step is that of transmitting a pulse of energy along a path which is transverse to the wall being measured. This is illustrated by the path 33 indicated in FIG. 1. The pulse to be transmitted will be one generated by the transducer 25 half of which is reflected from the surface 30 to change direction by 90° and so travel toward the wall 21 in a direction transverse thereto.

Another step is that of receiving reflected pulses after reflection of the transmitted pulse from the surfaces of the wall being measured, in order to determine the thickness of the wall. This is illustrated in FIG. 1 by the paths 33 and 29 over which the returning reflected acoustic energy pulses will go in travelling back to impinge upon the crystal 25. The crystal generates signals representative of such pulses. This is indicated in FIG. 2 where the time difference between the returning or reflected pulses 41 and 42, will be a measure of the thickness of the wall 21.

Another step is that of transmitting a separate pulse of energy along a path having angle of incidence, relative to the wall being measured, that is greater than the critical angle of refraction for the material of that wall. This is carried out by the splitting of the acoustic pulse which is transmitted from the transducer 25. The half that is thus split off is reflected from the surface 45, and then travels over the path 47. This energy pulse wil penetrate the wall 21 of the pipe, and if it encounters a discontinuity such as the cavity 51 illustrated, there will be a reflected pulse returned along the same path 47 and back along path 46 to the transducer 25.

Then a final step is that of receiving the other pulse reflection, if it appears, in order to characterize the presence of an anormaly. This is illustrated by the delayed reflected pulse e.g. pulse 57 of FIG. 2, which returns along paths 47 and 46 to the transducer 25. The arrival will be at a time spaced from the first reflected pulses since the length of the paths of travel is greater.

The method may also be described in a more comprehensive manner which relates to the multiple transducer arrangement such as that illustrated in FIGS. 11, 12 and 13. The steps of such method include the following.

First, the step of generating a plurality of single pulses sequentially, as described in connection with FIG. 13. These are directed along paths that are parallel to the axis of the pipe. Thus, in the FIG. 11 one of the transducers 105 is shown mounted on the body of an instrument 101. It is oriented so as to direct the pulses in a path parallel to the axis of the pipe 102. Generation of each pulse may be carried out as described in connection with FIG. 13. The triggering of an SCR 125 will create a discharge of the capacitor 128 across a path which includes the crystal 119. Consequently, an electrical pulse is applied, which creates the piezoelectric affect so as to produce an acoustic pulse output.

Then there are the steps of reflecting a portion of each of the single pulses from a 45° surface to direct them along paths transverse to the pipe wall. FIGS. 11 and 12 illustrate this step in that the pulse energy travelling down from transducers 105 is reflected by surface 106 and then goes in a direction transverse to the wall 102 of the pipe, i.e. over the path 109.

Another step is that of reflecting another portion of each single pulse from a surface more than 45 degrees relative to said parallel path. This step is illustrated in FIGS. 11 and 12 by the path 113, which is the path of travel for that portion of the pulse travelling down from transducers 105 that is reflected from the surface 112.

Another step is that of receiving reflected pulses which are returned from the transverse directed energy, in order to determine the thickness of the pipe wall. This is carried out by the conventional circuit controls for having the crystal 119 (of the transducer which has just transmitted its single pulse) connected in a receiver circuit for amplifying generated electrical signals that are caused when the crystal is deformed by the reflected pulse energy returning to it. The earliest reflected pulses returning will be those over the transverse paths 109 and these provide an indication of the thickness of the pipe wall 102.

Finally there is the step of receiving any reflected pulses which return from the other portion of the split single pulse that was transmitted from the transducer in order to determine whether there is a discontinuity of the pipe of the type which will reflect and return some of this angular energy. This is carried out by maintaining the crystal ciruit available for amplifying any reflected energy long enough to have a signal generated if the delayed returned reflected pulse exists.

While the foregoing preferred embodiments of the invention have been described above in considerable detail, in accordance with the applicable statutes, this is not to be taken as in any way limiting the invention but merely as being descriptive thereof.

We claim:

1. In a pulse-echo system for measuring wall thickness of pipes or the like, the improvement comprising in combination,
   means for generating a single pulse directed along a path that is longitudinal relative to said pipe wall,
   means for splitting said single pulse to form first and second named pulses,
   said splitting means comprising first and second reflecting surfaces,
   said first reflecting surface having an angle relative to said longitudinal path such that said first named pulse is directed transversely relative to said pipe wall for making said wall thickness measurement,
   said second reflecting surface having an angle relative to said longitudinal path such that said second named pulse is directed at an angle of incidence relative to said wall that is greater than the critical angle of refraction in order to permit any reflected energy from a discontinuity in said wall to be returned along the same path,
   said second reflecting surface being non-contiguous with said first reflecting surface and having an offset along said longitudinal path for causing a time delay of said second pulse relative to said first pulse, and
   means for receiving any reflected pulses from both said first and second named pulses whereby said wall thickness may be measured and any discontinuity may be characterized.

2. In a pulse-echo system according to claim 1 wherein
   said single pulse path direction is parallel to said wall, and
   said splitting means comprises means for reflecting a portion of said single pulse from a 45° angled surface, and means for reflecting another portion from a surface angled at more than 45° relative to said parallel path.

3. In a pulse-echo system for measuring wall thickness of a pipe according to claim 2, wherein said improvement further comprises
   a plurality of said single pulse genrating means located spaced peripherally about the axis of said pipe,
   and wherein said splitting means for reflecting portions of said single pulses is annular and comprises said angled surfaces spaced axially at predetermined different distances from said pulse generating means.

4. In a pulse-echo system for measuring wall thickness of a pipe, the improvement comprising in combination
   a plurality of pulse generating means located spaced peripherally about the axis and inside of said pipe,
   said means being oriented for directing the pulses parallel to the axis of said pipe,
   a first annular reflecting surface have a 45 ° angle relative to said axis and spaced axially from said plurality of pulse generating means,
   said first surface extending radially about half the width of said pulses for splitting off a portion of each and directing said portion along a path transverse to the wall of the pipe at that location,
   a second annular reflecting surface having an angle of more than 45° relative to said axis and being spaced axially at a greater distance from said pulse generating means than said first annular surface,
   said second surface being non-contiguous with said first surface and having an offset axially therefrom to provide said greater distance and to cause a time delay of the remaining portions of said pulses, and
   said second surface extending radially the other half of the width of said pulses for directing another portion of each pulse along a path having an angle of incidence relative to the wall of said pipe at that location which is greater than the critical angle of refraction in order to permit any reflected energy from a discontinuity in said wall to be returned along said other portion path.

* * * * *